US 8,654,335 B2

United States Patent
Hager et al.

(10) Patent No.: US 8,654,335 B2
(45) Date of Patent: Feb. 18, 2014

(54) METHOD AND DEVICE FOR QUANTIFICATION OF GASES IN PLUMES BY REMOTE SENSING

(71) Applicant: Hager Environmental and Atmospheric Technologies, LLC, Knoxville, TN (US)

(72) Inventors: J. Stewart Hager, Knoxville, TN (US); Geoffrey Yerem, Knoxville, TN (US)

(73) Assignee: Hager Environmental and Atmospheric Technologies, LLC, Knoxville, TN (US)

( * ) Notice: Subject to any disclaimer, the term of this patent is extended or adjusted under 35 U.S.C. 154(b) by 0 days.

(21) Appl. No.: 13/689,406

(22) Filed: Nov. 29, 2012

(65) Prior Publication Data

US 2013/0100451 A1 Apr. 25, 2013

Related U.S. Application Data

(63) Continuation-in-part of application No. 12/883,621, filed on Sep. 16, 2010, now Pat. No. 8,330,957, which is a continuation-in-part of application No. 12/493,634, filed on Jun. 29, 2009, now Pat. No. 8,134,711.

(51) Int. Cl.
G01N 21/00 (2006.01)

(52) U.S. Cl.
USPC ............................................ 356/438

(58) Field of Classification Search
USPC ............................................ 356/432, 438
See application file for complete search history.

(56) References Cited

U.S. PATENT DOCUMENTS

| | | | | |
|---|---|---|---|---|
| 4,924,095 A | * | 5/1990 | Swanson, Jr. | 250/338.5 |
| 5,319,199 A | * | 6/1994 | Stedman et al. | 250/338.5 |
| 5,489,777 A | * | 2/1996 | Stedman et al. | 250/338.5 |
| 5,498,872 A | * | 3/1996 | Stedman et al. | 250/338.5 |
| 6,455,851 B1 | * | 9/2002 | Lord et al. | 250/338.5 |
| 7,183,945 B2 | * | 2/2007 | DiDomenico et al. | 340/937 |
| 7,952,047 B2 | * | 5/2011 | Gevelber et al. | 219/121.47 |
| 8,330,957 B2 | * | 12/2012 | Hager | 356/438 |
| 2004/0104345 A1 | * | 6/2004 | Kansakoski et al. | 250/338.5 |
| 2007/0164220 A1 | * | 7/2007 | Luk | 250/338.5 |
| 2008/0297360 A1 | * | 12/2008 | Knox et al. | 340/628 |

OTHER PUBLICATIONS

Daniel A. Burgard et al., Spectroscopy Applied to On-Road Mobile Source Emissions, Applied Spectroscopy, 2006, 135A-148A, vol. 60, No. 5.

* cited by examiner

Primary Examiner — Roy M Punnoose
(74) Attorney, Agent, or Firm — Morris, Manning & Martin, LLP; Tim Tingkang Xia, Esq.

(57) ABSTRACT

Method and device for quantifying ingredients of a plume. In one embodiment, the method includes sweepingly directing a beam of light through the plume to a surface on which the beam of light is scattered, acquiring the scattered light scattered from the surface, and processing the acquired scattered light to determine an amount of ingredients of the plume. In one embodiment, the height of the back of the vehicle is measured as the top of the plume for calculating the total mass-per-distance of the plume. In another embodiment, by comparing the absorption spectrum of the plume and the background absorption spectrum of which no plume exists, the non-methane hydrocarbons (NMHC) of the plume emitted from a vehicle can be quantified.

18 Claims, 6 Drawing Sheets

METHOD AND DEVICE FOR QUANTIFICATION OF GASES IN PLUMES BY REMOTE SENSING

CROSS-REFERENCE TO RELATED PATENT APPLICATIONS

This application is a continuation-in-part of U.S. patent application Ser. No. 12/883,621, filed Sep. 16, 2010, entitled "DEVICE AND METHOD FOR QUANTIFICATION OF GASES IN PLUMES BY REMOTE SENSING," by J. Stewart Hager, now allowed, which itself is a continuation-in-part of U.S. patent application Ser. No. 12/493,634, filed Jun. 29, 2009, entitled "DEVICE FOR REMOTE SENSING OF VEHICLE EMISSION," by J. Stewart Hager, now U.S. Pat. No. 8,134,711. Each of the above disclosures is incorporated herein in its entirety by reference.

Some references, which may include patents, patent applications and various publications, are cited and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference were individually incorporated by reference.

FIELD OF THE INVENTION

The invention generally relates to remote detection of emission, and more particularly to method and device that utilize optical masses for quantifying ingredients of a plume emitted from a vehicle.

BACKGROUND OF THE INVENTION

It is known that vehicle emissions are a major contributor to air pollution. In order to identify vehicles that are releasing excessive polluting emissions, many countries mandate annual vehicle emission inspections. To this purpose various vehicle emission inspection systems have been developed. Generally, these systems can be very expensive, and their operation can require a vast amount of labor and skill. Additionally, emission inspection systems have traditionally been operated in testing stations where the emissions are measured when the test vehicle is idling or running under artificially loaded conditions. Although such measurements provide general baseline information regarding a vehicle's emissions and state of repair, it is not necessarily representative of "real world" driving conditions.

Figure 6:
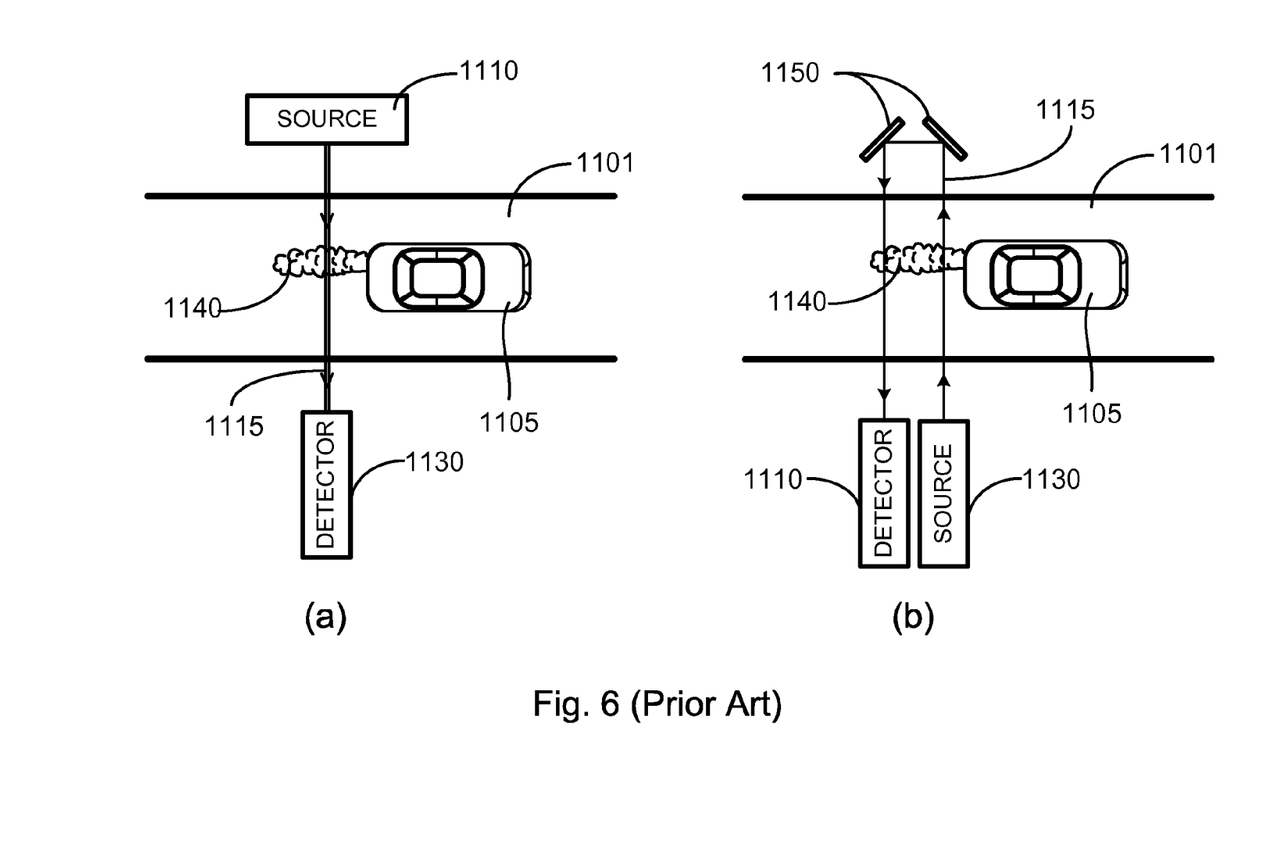
FIG. 6 shows schematically a conventional device for remote sensing of vehicle emission.

Recently, remote emission sensing systems have been developed for detecting emissions of vehicles as they are driving on the road. For example, U.S. Pat. Nos. 5,319,199 and 5,498,872 to Stedman et al. discloses a remote sensing system in which the light source 1110 and detector 1130 are oppositely located on both sides of the road 1101, respectively, as shown in FIG. 6(a). For such an arrangement, a beam of light 1115 generated from the source 1110 passes through an exhaust plume 1140 emitted from a vehicle 1105 driven on the road 1101, thereby carrying an absorption signal associated with components and concentrations of the exhaust plume 1140. The beam 1115 is collected by the detector 1130 for analyzing the components and concentrations of exhaust plume 1140. Alternatively, as shown in FIG. 6(b), the light source 1110 and detector 1130 are located on the same side of the road 1101. And two reflectors 1150 located on the opposite side of the road 1101 are used to reflect the beam 1115 generated from the source 1110 to the detector 1130 with two passes through the vehicle exhaust plume 1140, which increases the absorption signal. This system measures only part of the plume and has to ratio the $CO_2$ measurements to all other pollutants to get relative values. It does not measure the amount left behind or absolute values.

However, for such remote emission sensing systems, the source, detector and reflectors are set up on both sides of the road, and much care needs to be taken during their installation and maintenance. Additionally, such a system is difficult to operate with more than one lane of traffic particularly when more than one vehicle passes through the detector simultaneously. In other words, if multiple vehicles are present at the sensing location, each vehicle's exhaust plume may contribute equally to the emission measurement. Thus, on a single lane road, such as entrance and exit ramps, the existing remote sensing systems are not able to detect more than one exhaust plume at a time.

Furthermore, with current remote sensing systems the precision of the measurement can also depend on the position of the beam of light going across the road since the location of the vehicle's one or more exhaust pipes can vary from vehicle to vehicle. The precision of the emissions measured will vary depending on whether the beam is at the height of the tail pipe, or lower or higher where the exhaust has time to dilute before detection. With such an arrangement is also possible to miss the exhaust plume altogether.

Ultimately, the main drawback to current remote emission sensing is that since it only measures a portion of an exhaust plume it can only determine a plume's constituent gases and their relative concentrations. While such results can indicate if a vehicle is in need of repair, existing systems are not able to measure absolute amounts of emission components. Measuring absolute amounts of components is important since a surfeit can lead to severe air pollution. It is for this reason that many countries statutorily limit the amount of gas pollutants allowed in emissions. In fact, state and federal vehicle emissions standards and control requirements are stated in "grams per mile." With existing systems this value must be extrapolated from the ratios reported by identifying the vehicle make and model and making assumptions about whether the vehicle is running rich or lean, the load on the vehicle, etc.

Quantitative imaging of gas emissions techniques has been patented. For example, U.S. Pat. No. 5,319,199 describes an elaborate system which uses gas self-emission radiation and gas filled cells. Unfortunately, the complexity of this method is unnecessary and cost prohibitive.

Therefore, a heretofore unaddressed need exists in the art to address the aforementioned deficiencies and inadequacies.

SUMMARY OF THE INVENTION

In one aspect, the invention relates to a method for quantifying ingredients of a plume. In one embodiment, the method includes the steps of sweepingly directing a beam of light through the plume to a surface on which the beam of light is scattered; acquiring the scattered light scattered from the surface; and processing the acquired scattered light to determine an amount of ingredients of the plume.

In one embodiment, the processing step comprises the step of calculating an effective width, $w_i$, of each sweeping light beam, wherein the effective width $w_i$ satisfies with the relationship of:

$$w_i = \frac{1}{2}\theta_i \cdot (2r_i + l),$$

wherein $\theta_i$ is an angle of the light beam relative to a direction perpendicular to the road surface, $r_i$ is a distance between the light source and the top of the plume, and $l$ is a thickness of the plume. In one embodiment, the thickness l of the plume is corresponding to a height of the rear of the vehicle that emits the plume. The total mass-per-distance of the plume satisfies with the relationship of:

$$d_{Total} = \sum_i^N w_i \cdot x_i$$

wherein $x_i$ is an optical mass at each light beam passing through the plume.

In one embodiment, the directing step is performed with a Galvanometer.

In one embodiment, the acquired scattered light is processed in terms of an absorption spectrum of the plume. In addition, the method may also include the step of obtaining a background absorption spectrum of which no plume exists. By comprising the step of comparing the absorption spectrum of the plume and the background absorption spectrum, the non-methane hydrocarbons (NMHC) of the plume are quantified.

In another aspect, the invention relates to a device for quantifying ingredients of a plume. In one embodiment, the device has a light source for emitting a beam of light through the plume to a surface on which the light is scattered; a detector for acquiring the scattered light scattered from the surface; and a processor for processing the acquired scattered light to determine an amount of ingredients of the plume.

In one embodiment, the processor is configured to perform the function of calculating an effective width, $w_i$, of each sweeping light beam, wherein the effective width $w_i$ satisfies with the relationship of:

$$w_i = \frac{1}{2} \theta_i \cdot (2r_i + l),$$

wherein $\theta_i$ is an angle of the light beam relative to a direction perpendicular to the road surface, $r_i$ is a distance between the light source and the top of the plume, and l is a thickness of the plume. The thickness l of the plume is corresponding to a height of the rear of the vehicle that emits the plume. The total mass-per-distance of the plume satisfies with the relationship of:

$$d_{Total} = \sum_i^N w_i \cdot x_i$$

wherein $x_i$ is an optical mass at each light beam passing through the plume.

In one embodiment, the processor is configured to perform the function of obtaining an absorption spectrum of the plume. By comparing the absorption spectrum of the plume and a background absorption spectrum of which no plume exists, the non-methane hydrocarbons (NMHC) of the plume can be quantified.

In one embodiment, the device also has a positioning optics for sweepingly directing the beam of light through the plume to the surface on which the beam of light is scattered. In one embodiment, the positioning optics comprises a Galvanometer.

In one embodiment, the light source comprises one or more coherent light sources. The light source comprises a tunable laser.

These and other aspects of the invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, wherein.

DETAILED DESCRIPTION OF THE INVENTION

The invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about", substantially, or "approximately" shall generally mean within 20 percent, preferably within 10 percent, and more preferably within 5 percent of a given value or range. Numerical quantities given herein are approximate, meaning that the term "around", "about", substantially, or "approximately" can be inferred if not expressly stated.

As used herein, the term "LIDAR" is an acronym or abbreviation of "light detection and ranging", and is an optical remote sensing technology that measures properties of scattered light to find range and/or other information of a distant target. Differential Absorption LIDAR (DIAL) is a commonly used technique to measure column abundances of gases in the atmosphere.

As used herein, the term "EDAR" is an acronym or abbreviation of "emission detection and reporting", and is an emission sensing technology that measures properties of emission to find range and/or other information of a distant emission.

As used herein, the term "optical mass" is a measure of the total number of absorbing molecules per unit area occurring along the direction of propagation of the radiation in a gas sample.

As used herein, the terms "comprising," "including," "having," "containing," "involving," and the like are to be understood to be open-ended, i.e., to mean including but not limited to.

The description will be made as to the embodiments of the invention in conjunction with the accompanying drawings in FIGS. 1-5. In accordance with the purposes of this invention, as embodied and broadly described herein, this invention, in one aspect, relates to method and system that utilizes the EDAR technology to detect emissions of a vehicle as well as the amount of the pollutants emitted from the vehicle.

With the EDAR system, the beam of light emitted from a source is directed downwards, passing through the exhaust plume, toward the surface of a traffic lane of a road on which the vehicle is driven. The transmitted light is then scattered at the surface of the traffic lane. The EDAR system collects the scattered light from the surface of the traffic lane for the detector to receive. Because of the geometry of the remote sensing set up, the EDAR system is always looking down onto the whole plume. This allows the EDAR system to remote sense the entire plume at one time. Further, one can use the optical mass of each measurement across the plume to calculate absolute values. In one embodiment, the height of the back of the vehicle is measured as the top of the plume for calculating the total mass-per-distance of the plume. In another embodiment, by comparing the absorption spectrum of the plume and the background absorption spectrum of which no plume exists, the non-methane hydrocarbons (NMHC) of the plume emitted from a vehicle can be quantified.

Calculating the absolute value of a plume from the optical mass in one column (or cylinder) of gas is straightforward, which is the production of the optical mass multiplied by the area of the column perpendicular to the direction of the beam. For example, if the optical mass is in units of molecules/cm$^2$, and the area perpendicular to a circular column is $\pi r^2$ cm$^2$. Therefore, the amount of molecules and the column is just an optical mass multiplied by $\pi r^2$.

Figure 1:
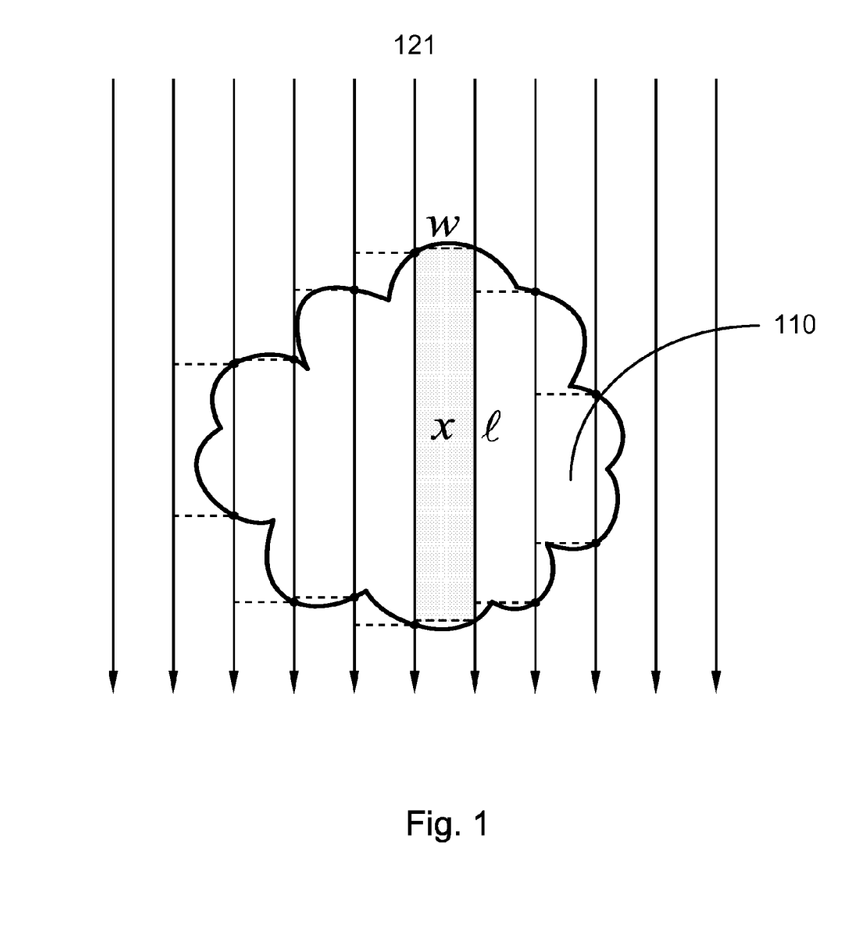
FIG. 1 illustrates schematically a method for quantifying absolute amounts of ingredients of a plume sampled with a discrete number of equispaced, infinitesimally thin beams of parallel light according to one embodiment of the invention.

As shown in FIG. 1, if a plume 110 is sampled with a discrete number of equispaced, infinitesimally thin beams of parallel light 121, the mass-per-distance, d, associated with a beam is estimated by taking its measured optical mass, x, and multiplying it by the beam spacing, w, $$d = w \cdot x, \quad (1)$$

$$x = C \cdot \frac{n}{V} \cdot l. \quad (2)$$

The total mass-per-distance of the plume is then determined by combining each value of d as a Reimann sum:

$$d_{Total} = \sum_{i}^{N} w \cdot x_i = Nw \cdot \frac{1}{N} \sum_{i}^{N} x_i = w_{Total} \cdot x_{Avg}.$$

Figure 2:
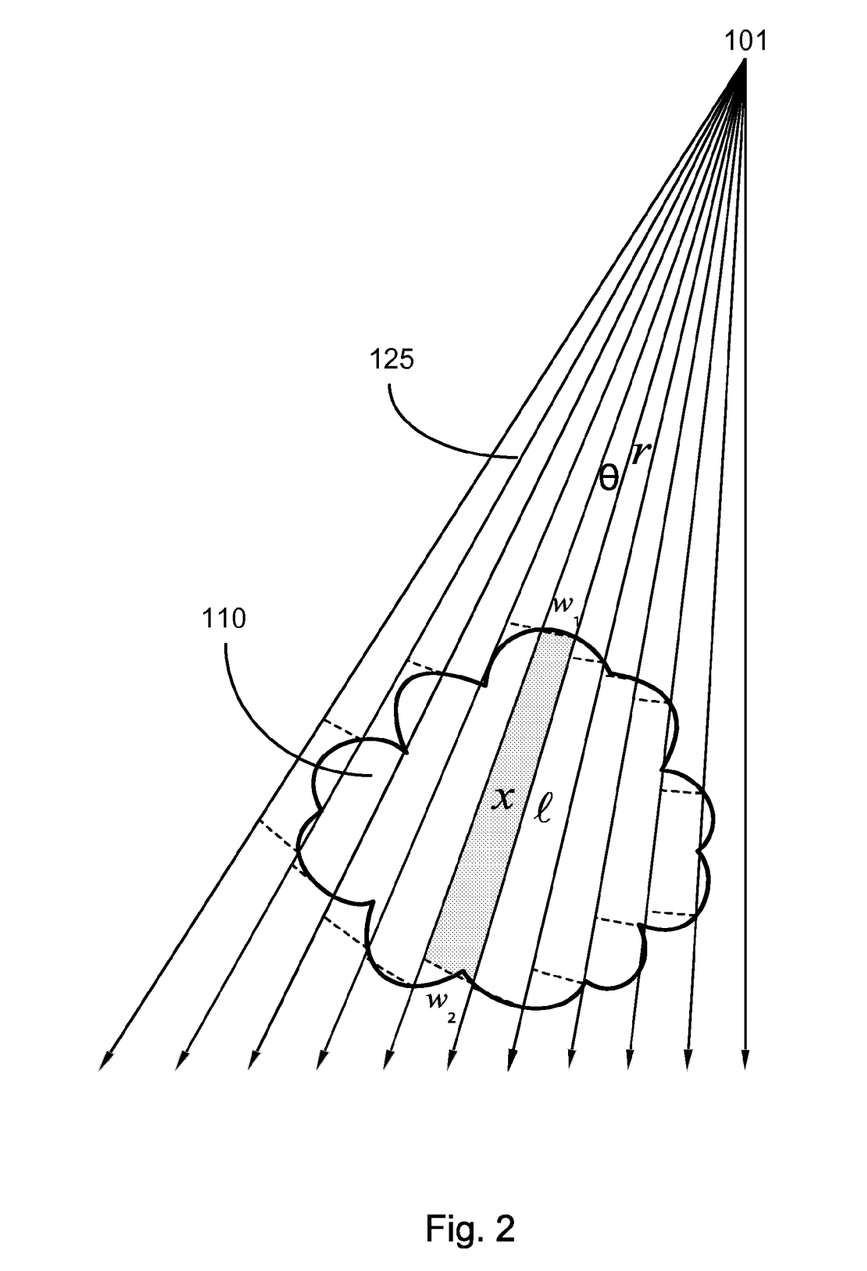
FIG. 2 illustrates schematically a method for quantifying absolute amounts of ingredients of a plume sampled with rays of a light beam according to one embodiment of the invention.

However, in the EDAR system, it scans the road from one point above the road. This in turn creates a cone-type geometry of a light beam, as shown in FIG. 2. Calculating the absolute values of the plume using cones instead of columns (cylinders) may become problematic because the area perpendicular to the propagation of the beam is different depending on where it is on the cone. It would be easier if the top of the plume 110 would be known. One could then find the average perpendicular area w of the cone. The average area w would be chosen at that point and the absolute value could be calculated. According to the invention, an average area w somewhere in the middle of the plume 110 is chosen.

As shown in FIG. 2, the same plume 110 is sampled with rays of light 125 originating at a focus (light source) 101. An effective value of the beam spacing (cross-sectional area) w is adapted to multiply the measured optical mass x, so as to obtain the mass-per-distance of the plume 110 that should be the same as that, as expressed in equation (1), in the parallel light beam shown in FIG. 1.

In the exemplary embodiment shown in FIG. 2, the mass-per-distance d for the plume 110 that is mostly uniform over the path length l is obtained by multiplying the density of the gas by the area w between the rays 126 that is filled by the plume 110.

$$d = w \cdot x = C \cdot \frac{n}{V} \cdot \left[ \frac{1}{2} \theta \cdot (r+l)^2 - \frac{1}{2} \theta \cdot r^2 \right]. \quad (3)$$

Insertion of the optical mass x in equation (2) into equation (3) results in the following relationships:

$$w \cdot C \cdot \frac{n}{V} \cdot l = C \cdot \frac{n}{V} \cdot \frac{1}{2} \theta \cdot [(r+l)^2 - r^2], \text{ and} \quad (4)$$

$$w = \frac{1}{2} \theta \cdot (2r+l)$$

Accordingly, the effective width w is the width between the rays 125 at a distance from the focus 101 to a halfway between the extents of the plume 110.

As an example, assuming that
θ=0.68 mrad,
r=14 ft,
l=4 in,
then
w=0.116 in,
if r=13 ft, w=0.108 in, Δw=−7%,
if r=15 ft, w=0.123 in, Δw=+7%, $$\Delta w = \frac{r + \Delta r - r}{r} = \frac{\Delta r}{r}.$$

Therefore, to minimize the error, the light source 101 needs to be substantially far away from the plume 110.

Figure 3:
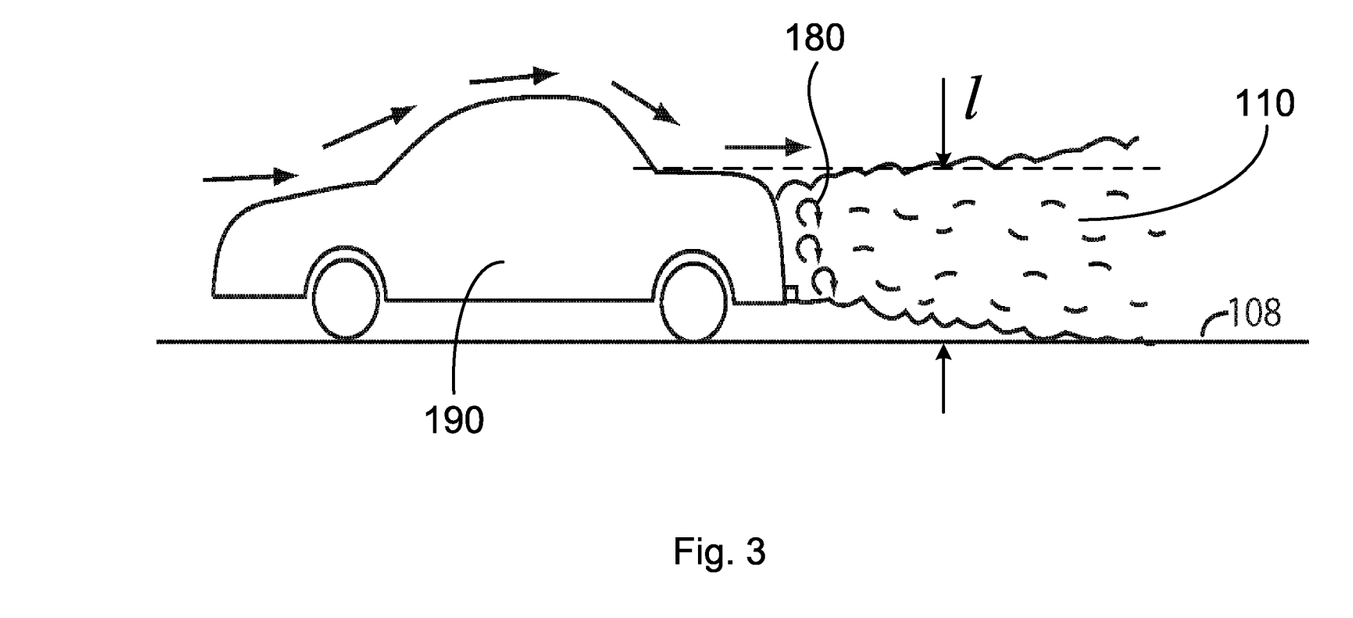
FIG. 3 shows schematically a vehicle and a plume emitted therefrom.

In addition, the air flowing over a vehicle 190 creates a vortex 180 behind the vehicle 190, as shown in FIG. 3. This vortex 180 mixes the exhaust plume 110. It is known that the top of the plume 110 cannot be much higher than the top of the trunk or roof of the vehicle, just as the vehicle 190 passes. According to the invention, the height of the back of the vehicle 180 is used as an approximation for the distance l from the road surface 108 to the top of the plume 110.

In one aspect, the invention relates to a method for quantifying ingredients of a plume. In one embodiment, the method includes the steps of sweepingly directing a beam of light through the plume to a surface on which the beam of light is scattered; acquiring the scattered light scattered from the surface; and processing the acquired scattered light to determine an amount of ingredients of the plume.

In one embodiment, the processing step comprises the step of calculating an effective width, $w_i$, of each sweeping light beam, wherein the effective width $w_i$ satisfies with the relationship of:

$$w_i = \frac{1}{2}\theta_i \cdot (2r_i + l),$$

wherein $\theta_i$ is an angle of the light beam relative to a direction perpendicular to the road surface, $r_i$ is a distance between the light source and the top of the plume, and l is a thickness of the plume. In one embodiment, the thickness l of the plume is corresponding to a height of the rear of the vehicle that emits the plume. The total mass-per-distance of the plume satisfies with the relationship of:

$$d_{Total} = \sum_i^N w_i \cdot x_i$$

wherein $x_i$ is an optical mass at each light beam passing through the plume.

In one embodiment, the directing step is performed with a Galvanometer.

Additionally, if one knows the absolute value of a swath of the plume perpendicular to the direction of travel, then one can assume that the absolute amounts of the target molecules were once in the tailpipe at the same time. One can then use the ideal gas equation with ambient temperature (or approximate tailpipe temperature) and pressure to calculate the density, and therefore the number of molecules per unit volume of the air. The absolute amounts could be used to calculate the tailpipe concentrations using a typical 2 inch diameter tailpipe. Therefore, the tailpipe concentrations could be calculated without using stoichiometric equations, which are employed by conventional remote sensing devices to backtrack tailpipe concentrations.

Since there is a large amount of methane already in the earth's atmosphere and natural concentrations can be elevated in certain areas, it is important to separate methane from the other hydrocarbons coming out of the exhaust plume of a vehicle. In one aspect, the invention provides a method for calculating non-methane hydrocarbons in a plume emitted from a vehicle by resolving methane lines on the top of broad features of heavier hydrocarbons in absorption spectra of the plume.

What makes remote sensing with lasers so sensitive is that the narrow line width of a laser line is able to disseminate individual lines from a molecular rotational and vibrational transition. The difference in energy between two adjacent rotational transitions is proportional to the inverse of the moment of inertia of the molecule through the axis of rotation. Therefore, the smaller the moment of inertia about the axis of rotation is, the larger the spacing between rotational lines is.

In one embodiment, the method includes the steps of sweepingly directing a beam of light through the plume to a surface on which the beam of light is scattered; acquiring the scattered light scattered from the surface; and processing the acquired scattered light to determine an amount of ingredients of the plume. The acquired scattered light is processed in terms of an absorption spectrum of the plume. In addition, the method may also include the step of obtaining a background absorption spectrum of which no plume exists. By comprising the step of comparing the absorption spectrum of the plume and the background absorption spectrum, the non-methane hydrocarbons (NMHC) of the plume are quantified.

Figure 4:
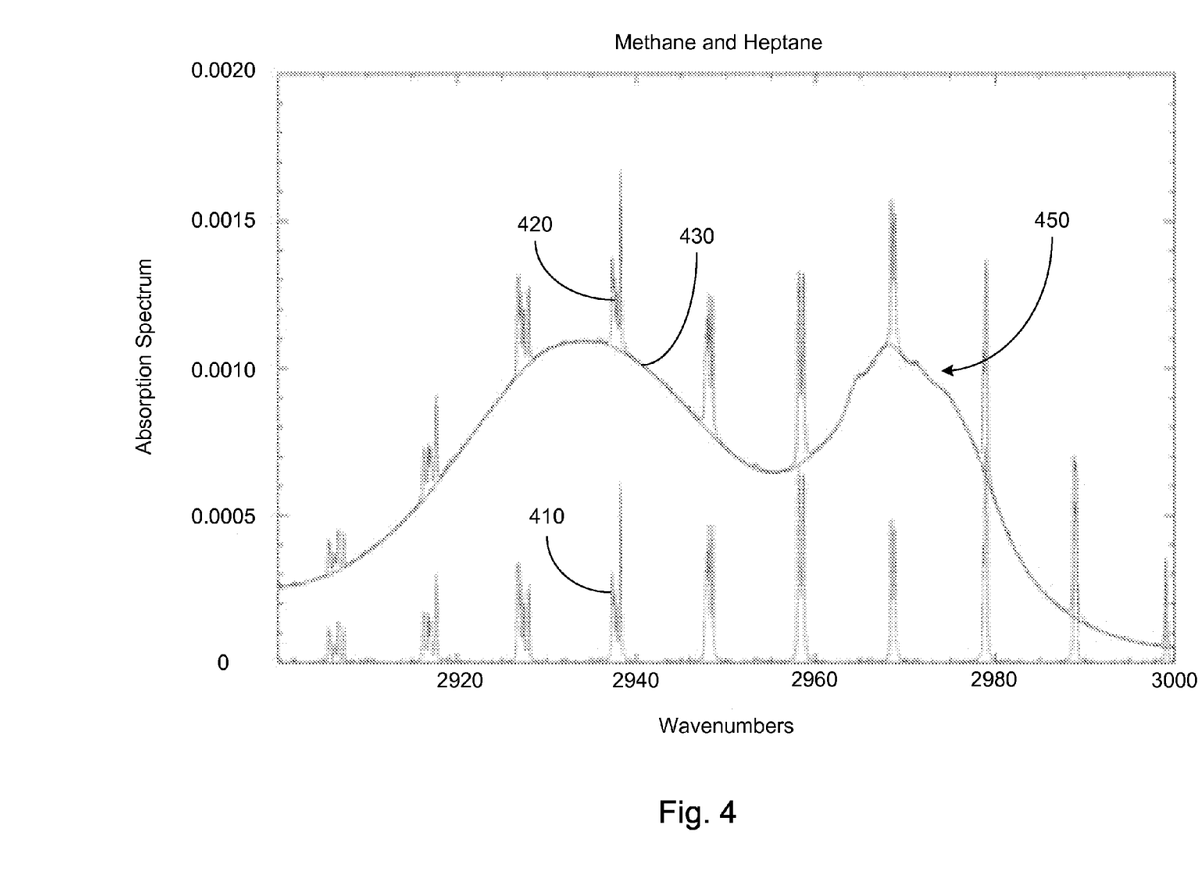
FIG. 4 shows the absorption spectra of methane and non-methane hydrocarbons in a plume emitted from a vehicle.

FIG. 4 is the absorption spectra of a plume emitted from a vehicle, which illustrates the difference between light hydrocarbon molecules, such as methane, and heavy hydrocarbon molecules, such as Heptane. The methane narrow lines 420 sit on the broad absorption feature 430 of heavier hydrocarbon molecule. The broad absorption feature 430 can be used as a baseline for the methane absorption without any loss of accuracy. Only if the heavier molecule has a sharp feature would it contribute to the absorption of the methane line. This would physically be impossible because the moment of inertia around any axis of the heavy molecule is large, and therefore, the rotational lines would be so close together that they would be unresolvable no matter the resolution of an instrument. Accordingly, one aspect of the invention relates to a method that utilizes the fact of the molecular physics to quantify non-methane hydrocarbons (NMHC).

In one embodiment, the method includes the following steps: at first, the background signal is measured during periods without traffic. This results in absorption 410 without contributions of heavy hydrocarbon molecules, which is corresponding to the absorption spectrum of methane that exists in the earth's atmosphere and natural concentrations. Then, the absorption signal 450 of an exhaust plume emitted from a vehicle is measured when the vehicle passes. Next, the signal 410 without traffic and the signal 450 from an exhaust plume are compared to quantify NMHC that exists in exhaust plume emitted from the vehicle. As shown in FIG. 4, the methane line 410 is measured for quantifying the NMHC from the exhaust plume. In the measurements of the absorption spectra 410 and 450, a laser is swept a cross the road on which the vehicle drives, at about 20 Hz, then, the exhaust gas is sampled by scanning the wavelength of the laser at 20 KHz. In one embodiment, as the laser sweeps it emanates from one point on the Galvanometer mirror, therefore creating the top of a cone. The Galvanometer collects the scattered light and directs it toward the collection mirror. The lighter hydrocarbon molecules coming from vehicle exhausts include ethane, ethylene and acetylene. The sharp features from these molecules can be measure separately or approximated. The avobe method is essentially the same method used with narrow bandwidth filters, as disclosed in U.S. patent application Ser. No. 12/883,621, which is incorporated herein in its entirety by reference.

Figure 5:
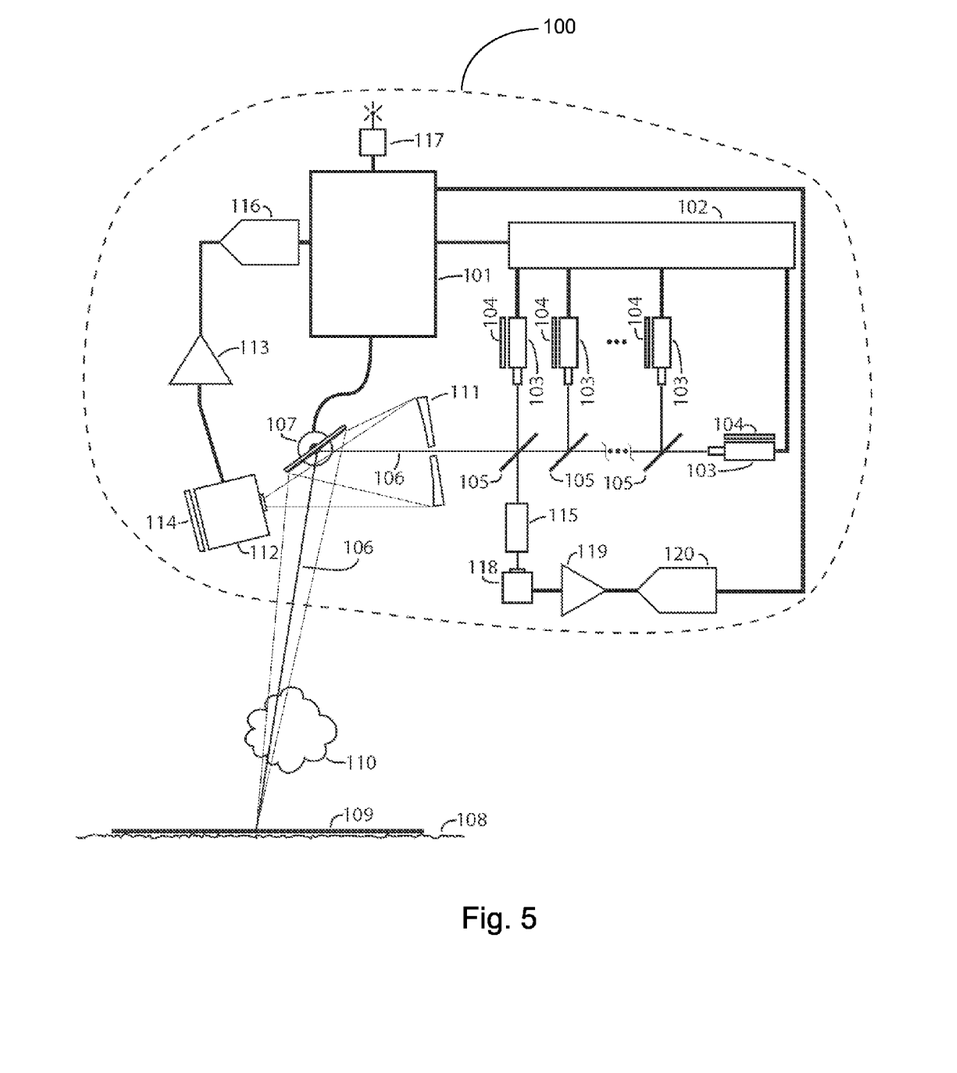
FIG. 5 shows schematically a device for scanning a laser across the roadway according to one embodiment of the invention.

Referring to FIG. 5, a device 100 for quantifying non-methane hydrocarbons in an exhaust plume is shown according to one embodiment of the invention. The device 100 includes coherent light sources or lasers 103, or a tunable laser, and a single-element detector 112. One or more coherent light sources 103 emitting at different selected wavelengths are time-modulated at the laser signal driver and TEC controller 102 by a controller 101. In the case of tunable diode lasers, the wavelengths can be selected by setting the temperature of each laser 103 with a corresponding cooling device 104. In one embodiment, the coherent light sources 103 are the DFB Continuous wave lasers that scan over a small range of wavelengths at usually 20 KHz. Therefore, a measurement is made every $\frac{1}{1000}$ of a sweep. The cooling device 104 is the TEC to cool the lasers 103. The resulting time-modulated light beams are combined with Beamsplitters and/or mirrors 105, and are sent through positioning optics 107. In one embodiment, the positioning optics 107 is a Galvanometer with a mirror on top that sweeps across the road 108 at usually 20 Hz. The Galvanometer is also adapted to collect the scattered light and directs it toward the collection mirror 111. The positioned light beam 106 passes through a gaseous plume 110, reflecting off of some substantially reflective material 109. The reflected light beam 106 passes through detection optics 111 and is focused into an opto-electronic detector 112. The electric signal from the detector 112 passes into a low-noise amplifier 113. The detector 112 as well as the amplifier 113 can be placed in a cooling mechanism 114 to increase the sensitivity and stability of the detection. The resulting signal is then passed into an analog-to-digital converter 116. Ultimately the measurement is digitized and processed by the controller 101. The results can be locally displayed or recorded as well as transmitted to a remote location by some communication mechanism 117.

The controller 101 can be a computing device such as an embedded computer in conjunction with application specific digital electronics such as a Field Programmable Gate Array (FPGA).

The coherent sources 103 are typically cooled by a cooling mechanism 104. The cooling mechanism 104 is typically a thermo-electric cooler in conjunction with a temperature measurement device such as a thermistor, which allows the temperature of the source 103 to be precisely controlled electronically with a feedback control system, for example. Adjusting the temperature allows some lasers to be tuned for wavelength. Controlling the temperature has the added benefit of avoiding temperature drift, which can inadvertently modulate the source 103. If the source 103 is substantially stable at a desired wavelength, the cooling mechanism 104 can be omitted simplifying the design as well as lowering its cost.

Since wavelengths of tunable lasers can be swept over many absorption peaks, the controller 101 can pick a peak, which maximizes the signal-to-noise ratio. Usually, it will be a wavelength with the largest absorption and the lowest temperature sensitivity for the measured gas while not coinciding with any other present gases. Also, the system can pick a different wavelength in case it detects is some form of interference at the existing wavelength.

The output power of each coherent source 103 can be regulated as well. This can be done with a current feedback system or a photo-diode feedback system or a combination of the two.

The sources can be modulated by direct electrical stimulation 102 or mechanically using an electrically controlled shutter such as a chopper wheel or a liquid crystal shutter. One method of modulating the light source 103 in the time domain is using a constant frequency waveform such as a sine wave or square wave as well as other more complex, orthogonal patterns. Other time-domain modulation techniques, such as shifting the phase between two sources by 90 degrees, are possible as well.

Time-modulation of the coherent light sources allows the system to ignore background signals or noise by picking a modulation which avoids external light sources. This not only includes any ambient light sources, but also any light emitted by the hot gaseous plume itself. The transmission of light through a plume can be then be consistently measured regardless of the temperature of the plume. Time-modulation also allows the invention to use a single detector 112 by placing each light signal in its own frequency band which can be separated electronically by a demodulation mechanism 115. This reduces the physical complexity of the design as well as replacing high-cost exotic light detection materials with low-cost demodulation electronics or digital computation. Additionally, time-modulation increases the sensitivity of the detector 112 by operating in a band where 1/f noise is lower.

If the coherent light sources 103 are not modulated separately in the time domain, other means can be used to detect each source. For example, the system can use multiple detectors, each tuned to a specific optical wavelength, one for each coherent source. One method is to use an optical filter in conjunction with each detector or even use the detector's natural bandwidth to discriminate each light source. Another method involves changing the polarization of each source and using detectors in conjunction with polarization filters.

The function of the optical combiner 105 is to form the separate coherent beams from the sources 103 into a single light beam 106. The optical combiner 105 can be a fused set of fiber optics or a reversed beam splitter, for example. The optical combiner can be eliminated if only one measurement wavelength is desired or if the sources happen to already be in a single beam or if separate detectors 112 is used for each source 103.

Typically the positioning optics 107 is a spinning or an oscillating mirror connected to a speed-controlled motor, such as a galvanometer. The frequency of the scan determines how fast the light beam is scanned over an area of interest. Also, the amplitude of an oscillating mirror determines the field of view. Also, the galvanometer is inherently synchronized with the detection circuitry. The scan can be a single line 131 or a series of lines 141 in some pattern, which can be used to remotely detect the properties of the gaseous plume of interest. By scanning the light beam 106, the position of the gaseous plume 110 can be determined. Since the speed of the scanning apparatus 107 is controlled, the controlling device 101 can correlate the measurement of the detector 112 with the position of the beam 106.

The reflector 109 can be made of various materials. Retro-reflective tape or paint can be used, for example. Alternatively, an array of mirrored corner cubes can be attached to the roadway. Other aspects over the choice of material involve whether or not the installation is temporary or permanent. The additional reflector 109 can be omitted if the roadway 108 or other pre-existing background feature is substantially reflective so that a suitable signal-to-noise ratio is achieved with the plume 110 of interest. The reflective surface 109 can be omitted altogether if the source and detector are separated such that the plume 110 is between the two. This requires two separate controllers 101 and possible a phase-lock loop or other means to synchronize the two devices.

Since the reflective surface 109 is on a roadway 108 or some other uncontrolled area given to environmental wear-and-tear, it is reasonable to assume that the reflection will not be uniform over the area of the surface. Because this invention divides the measured region into substantially small beams 106, the reflection over any one beam 106 will be mostly constant. Also, since the measurements can be made relative to a baseline measurement 203, the constant sources of attenuation will divide out of the calculations.

Since this embodiment uses an external reflective surface 109, both the modulated sources 103 as well as the detector 109 can be physically together 118, and controlled by a single controller 101. One advantage of this scheme is that since the modulated sources and the detector can be controlled centrally, the modulated sources can be synchronized with the detector electronics. This eliminates the need for a phase-lock-loop or other synchronizing mechanism in the detector electronics.

The detection section of this embodiment includes focusing optics 111 as well as an electro-optical detector 112 connected to a low-noise amplifier 113. The focusing optics 111 allows the embodiment to image a large area, preferable large enough to see the entire plume of interest 110. The detector 112 can be a semi-conductor photodiode or a thermopile or any such sensitive detection device. The detector is made of a material that can detect light in the desired wavelengths. The low-noise amplifier 113 can consist of any appropriate analog signal processing electronics able to suitably extract the signal of interest from the detector 112.

Conventionally, parallel light sources are utilized to measure gaseous plumes, which is disadvantageous because it requires the measurement system to be as large as the plume itself. This can be impractical if the plume is very large such as one from a smoke stack. This embodiment of the invention uses focused light which allows the entire system 118 to be substantially smaller than the plume 110 itself or the region of interest and fit in a compact and practical space. This potentially makes the device unobtrusive and portable.

The opto-electronic detector 112 as well as the low-noise amplifier 113, can be cooled 114 to increase the sensitivity of the detection. Controlling the temperature has the added benefit of making the detector 112 more stable, eliminating unwanted drift in the measured signal. Various cooling techniques are possible including thermo-electric coolers, a Dewar flask containing some cryogenic liquid, or a Stirling engine. If the existing detector element 112 and the low-noise amplifier 113 are substantially sensitive enough, the cooling mechanism 114 can be omitted altogether saving cost and simplifying the design.

While using only single broadband detector 112 is desirable to keep the system simple, a series of narrow-band or otherwise band-limited detectors can be used if there isn't any one practical detector with contiguous band which contains all of the wavelengths of interest.

In sum, the invention, among other things, recites a remote sensing device that uses the EDAR technology. The beam of light emitted from a source is directed downwards, transmitting through the exhaust plume, toward the surface of a traffic lane of a road on which the vehicle is driven. The transmitted light is then scattered at the surface of the traffic lane. A collecting optics is used to collect the scattered light from the surface of the traffic lane. The collected light is delivered to the detector for analyzing the components and providing an amount of the determined component of the exhaust plume. In one embodiment, the height of the back of the vehicle is measured as the top of the plume for calculating the total mass-per-distance of the plume. In another embodiment, by comparing the absorption spectrum of the plume and the background absorption spectrum of which no plume exists, the non-methane hydrocarbons (NMHC) of the plume emitted from a vehicle can be quantified.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A method for quantifying ingredients of a plume, comprising the steps of:
    (a) sweepingly directing a beam of light through the plume to a surface on which the beam of light is scattered;
    (b) acquiring the scattered light scattered from the surface; and
    (c) processing the acquired scattered light to determine an amount of ingredients of the plume.

2. The method of claim 1, wherein the processing step comprises the step of calculating an effective width, $w_i$, of each sweeping light beam, wherein the effective width $w_i$ satisfies with the relationship of:

$$w_i = \frac{1}{2}\theta_i \cdot (2r_i + l),$$

wherein $\theta_i$ is an angle of the light beam relative to a direction perpendicular to the road surface, $r_i$ is a distance between the light source and the top of the plume, and $l$ is a thickness of the plume.

3. The method of claim 2, wherein the thickness $l$ of the plume is corresponding to a height of the rear of the vehicle that emits the plume.

4. The method of claim 3, wherein the total mass-per-distance of the plume satisfies with the relationship of:

$$d_{Total} = \sum_i^N w_i \cdot x_i$$

wherein $x_i$ is an optical mass at each light beam passing through the plume.

5. The method of claim 1, wherein the directing step is performed with a Galvanometer.

6. The method of claim 1, wherein the acquired scattered light is processed in terms of an absorption spectrum of the plume.

7. The method of claim 6, further comprising the step of obtaining a background absorption spectrum of which no plume exists.

8. The method of claim 7, further comprising the step of comparing the absorption spectrum of the plume and the background absorption spectrum so as to quantify non-methane hydrocarbons (NMHC) of a plume.

9. A device for quantifying ingredients of a plume, comprising:
    (a) a light source for emitting a beam of light through the plume to a surface on which the light is scattered;
    (b) a detector for acquiring the scattered light scattered from the surface; and
    (c) a processor for processing the acquired scattered light to determine an amount of ingredients of the plume.

10. The device of claim 9, wherein the processor is configured to perform the function of calculating an effective width, $w_i$, of each sweeping light beam, wherein the effective width $w_i$ satisfies with the relationship of:

$$w_i = \frac{1}{2}\theta_i \cdot (2r_i + l),$$

wherein $\theta_i$ is an angle of the light beam relative to a direction perpendicular to the road surface, $r_i$ is a distance between the light source and the top of the plume, and $l$ is a thickness of the plume.

11. The device of claim 10, wherein the thickness $l$ of the plume is corresponding to a height of the rear of the vehicle that emits the plume.

12. The device of claim 11, wherein the total mass-per-distance of the plume satisfies with the relationship of:

$$d_{Total} = \sum_i^N w_i \cdot x_i$$

wherein $x_i$ is an optical mass at each light beam passing through the plume.

13. The device of claim 9, wherein the processor is configured to perform the function of obtaining an absorption spectrum of the plume.

14. The device of claim 13, wherein the processor is configured to perform the function of comparing the absorption spectrum of the plume and a background absorption spectrum of which no plume exists, so as to quantify non-methane hydrocarbons (NMHC) of a plume.

15. The device of claim 9, further comprising a positioning optics for sweepingly directing the beam of light through the plume to the surface on which the beam of light is scattered.

16. The device of claim 15, wherein the positioning optics comprises a Galvanometer.

17. The device of claim 9, wherein the light source comprises one or more coherent light sources.

18. The device of claim 17, wherein the light source comprises a tunable laser.

* * * * *